(12) United States Patent
Toki

(10) Patent No.: US 7,544,858 B2
(45) Date of Patent: Jun. 9, 2009

(54) METHOD OF TRANSFORMING MONOCOTYLEDONOUS SEED

(75) Inventor: Seiichi Toki, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 10/594,130

(22) PCT Filed: Mar. 25, 2005

(86) PCT No.: PCT/JP2005/005592

§ 371 (c)(1),
(2), (4) Date: Jun. 27, 2007

(87) PCT Pub. No.: WO2005/092082

PCT Pub. Date: Oct. 6, 2005

(65) Prior Publication Data

US 2007/0256188 A1 Nov. 1, 2007

(30) Foreign Application Priority Data

Mar. 25, 2004 (JP) .............................. 2004-090639

(51) Int. Cl.
*C12N 15/82* (2006.01)
(52) U.S. Cl. ...................................... 800/294; 800/278
(58) Field of Classification Search ........................ None
See application file for complete search history.

(56) References Cited

U.S. PATENT DOCUMENTS

2005/0138694 A1   6/2005   Tanaka et al.

FOREIGN PATENT DOCUMENTS

| EP | 1 198 985 A1 | | 4/2002 |
|---|---|---|---|
| JP | 2001-029075 | | 7/1999 |
| JP | 2001-029075 | * | 2/2001 |
| WO | WO01/06844 A1 | | 2/2001 |

OTHER PUBLICATIONS

Park, H-D., et al. (1995). "Construction of Binary Vectors for the Rice Transformation *Using a Rice Actin Promoter and Replication Origin of pTi12 Isolated from Agrobacterium tumefaciens* KU12." J. Plant. Biol. 38(4):365-371. Jan. 1, 1995.

Toki, S. et al., "Early infection of scutellum tissue with Agrobacterium allows high-speed transformation of rice", *The Plant Journal*, 47:969-976 (2006).

The European Office Action/Supplemental European Search Report from European Patent Application EP 05 721 519.6, search report dated Feb. 23, 2009, 7 pages (2009).

Dale, P.J. et al., "Agroinfection of Wheat: Inoculation of In Vitro Growth Seedlings and Embryos", *Plant Science*, 63:237-245 (1989).

* cited by examiner

*Primary Examiner*—Cathy Kingdon Worley
(74) *Attorney, Agent, or Firm*—Susan J. Myers, Fitch; Peter J. Dehlinger; King & Spalding LLP

(57) ABSTRACT

Provided is a method of transforming a monocotyledon by using *agrobacterium*. There is provided a method of transforming a monocotyledon by using *agrobacterium* containing a desired recombinant gene. This transforming method comprises the steps of sowing a culture medium containing a plant growth factor with a monocotyledonous seed, conducting culturing for 1 to 3 days so as to effect germination and infecting the seed with *agrobacterium*. This method makes it feasible to rapidly transform monocotyledons, including a rice plant.

1 Claim, 6 Drawing Sheets pCAMBIA1390-sGFP

Photograph of GFP fluorescence on day 7 after selection

State of seed on day 7 after selection

Photograph of GFP fluorescence on day 14 after selection

State of seed on day 14 after selection

Photograph of GFP fluorescence on day 14 after redifferentiation

State of seed on day 14 after redifferentiation

Photograph of GFP fluorescence on day 7 after selection

State of seed on day 7 after selection

Photograph of GFP fluorescence on day 14 after selection

State of seed on day 14 after selection

Photograph of GFP fluorescence on day 14 after redifferentiation

State of seed on day 14 after redifferentiation

Photograph of GFP fluorescence on day 7 after selection

State of seed on day 7 after selection

Photograph of GFP fluorescence on day 14 after selection

State of seed on day 14 after selection

Photograph of GFP fluorescence on day 20 after redifferentiation

State of seed on day 20 after redifferentiation

Probes used for Southern Hybridization

METHOD OF TRANSFORMING MONOCOTYLEDONOUS SEED

TECHNICAL FIELD

The present invention relates to an *Agrobacterium*-mediated transformation method for monocotyledonous seeds.

BACKGROUND ART

One means for improving a plant includes a "transformation technique", whereby a desired recombinant gene for modifying a character is introduced into the plant. Efficient and quick transformation techniques are extremely important for the molecular breeding of useful plants, in particular grain crops, which are important staple foods.

A majority of grain crops (e.g., rice, wheat, barley, and corn) are classified as monocotyledons. Various transformation techniques for transforming monocotyledons have hitherto been developed. Transformation techniques are generally classified into direct transformation techniques and indirect transformation techniques.

Examples of direct transformation techniques include electroporation techniques (see Non-Patent Documents 1 and 2), particle gun techniques (see Non-Patent Document 3) and polyethylene glycol (PEG) techniques (see Non-Patent Document 4). Electroporation techniques and particle gun techniques have been generally used as methods for transforming monocotyledons which can achieve relatively efficient gene introduction.

An example of an indirect transformation technique is an *Agrobacterium*-mediated transformation technique (hereinafter, this may also be referred to as an "*Agrobacterium* transformation technique"). *Agrobacteria* are a species of plant pathogenic bacteria. *Agrobacteria* are characterized in that, when a plant is infected therewith, a T-DNA region which is present on the plasmids that *Agrobacteria* have (e.g., Ti or Ri plasmid) is incorporated into the plant. The *Agrobacterium* transformation technique utilizes the incorporation of the T-DNA region into plants as a means for introducing genes into plants. In short, a plant is infected with an *Agrobacterium* which contains a desired recombinant gene. After infection, the desired recombinant gene is transferred from the *Agrobacterium* into plant cells so as to be incorporated into the plant genome.

The *Agrobacterium* transformation technique is sufficiently established so far as dicotyledons are concerned. A large number of stable transformed plants have already been created which express desired recombinant genes.

On the contrary, it has conventionally been recognized as difficult to apply the *Agrobacterium* transformation technique to monocotyledons. For example, Portrykus et al. (Non-Patent Document 5) report that monocotyledons cannot be infected with *Agrobacteria*. On the other hand, a great deal of attempts have been made to transform monocotyledons by using *Agrobacteria*, which have shed light on the possibility of applying the *Agrobacterium* transformation technique to monocotyledons.

For example, Raineri et al. took the scutellum of rice, scarred it, and placed it on a medium which induces dedifferentiation; a few days later, the scutellum portion was infected with an *Agrobacterium*. As a result, although normally redifferentiated plant bodies were not obtained, calluses having a foreign gene introduced therein were successfully induced (see Non-Patent Document 6).

Japanese Patent No. 2649287 (Patent Document 1) discloses an *Agrobacterium* transformation technique for rice and corn. According to this method, it is necessary to employ cultured tissue (e.g., calluses), which are dedifferentiated, as a plant sample to be transformed by an *Agrobacterium*. Therefore, prior to infection with an *Agrobacterium*, it generally takes 3 to 4 weeks to induce dedifferentiation in order to produce dedifferentiated culture tissue from a plant sample to be transformed (e.g., a leaf section).

Japanese Patent No. 3141084 (Patent Document 2) discloses a transformation method for monocotyledons using germinated seeds which are germinated by being subjected to pre-culture with a medium containing 2,4-D for 4-5 days after sowing. When using the transformation method disclosed in Patent Document 2, monocotyledons can be transformed more quickly as compared to the transformation method described in Patent Document 1, and therefore, it is excellent. However, it was considered that, prior to infection with an *Agrobacterium*, pre-culture for about 4-5 days would still be required.

As described above, for the transformation of monocotyledons via an *Agrobacterium* according to conventional techniques, a long period of time is required to prepare plant tissue/plant cells, which can be infected with an *Agrobacterium* (e.g., callusing of monocotyledon cells). The time required for the aforementioned preparation has been a barrier to promoting the efficiency of molecular breeding of monocotyledon cells. Therefore, in order to build up molecular breeding, it is significantly important to reduce the time required for transformation.

Therefore, it is desired that a method for transforming plant cells more quickly than the conventional techniques be established.

Patent Document 1: Japanese Patent. No. 2649287
Patent Document 2: Japanese Patent No. 3141084
Non-Patent Document 1: Shimamoto K. et al., Nature, 338: 274-276, 1989
Non-Patent Document 2: Rhodes C. A. et al., Science, 240: 204-207, 1989
Non-Patent Document 3: Christou P. et al., Bio/Technology 9: 957-962, 1991
Non-Patent Document 4: Datta, S. K. et al., Bio/Technology, 8: 736-740, 1990
Non-Patent Document 5: Portrykus et al., BIO/TECHNOLOGY, 535-542, 1990
Non-Patent Document 6: Raineri, D. M. et al., Bio/Technology, 8: 33-38, 1990

DISCLOSURE OF THE INVENTION

Problems to be Solved by the Invention

The present invention is intended to solve the aforementioned problems. An objective of the present invention is to improve *Agrobacterium* transformation techniques for monocotyledons and provide a quicker transformation method compared to the conventional methods. According to the method of the present invention, it is possible to create a transformed plant far more efficiently and quickly than any conventional *Agrobacterium* transformation techniques.

Means for Solving the Problems

The present inventor has found that, contrary to conventional findings, seeds of monocotyledons, which have been cultured in the presence of a plant growth factor for 1 to 3 days, can be transformed via an *Agrobacterium*, and thus, the present invention was completed.

The present invention provides the following matters:

1. A method for transforming a monocotyledon, comprising a step of infecting a seed of the monocotyledon with an *Agrobacterium*, which contains a desired recombinant gene, wherein the seed is a germinated seed which is germinated by being subjected to pre-culture with a medium containing a plant growth factor for 1 to 3 days after sowing.

2. A method according to item 1, wherein the seed is an intact seed.

3. A method according to item 1, wherein the plant growth factor is auxin.

4. A method according to item 1, wherein the plant growth factor is 2,4-D.

5. A method according to item 1, wherein the monocotyledon is a plant of the family Gramineae.

6. A method according to item 5, wherein the plant of the family Gramineae is rice.

The present invention relates to a method for transforming monocotyledons, the method including a step of infecting an intact seed with an *Agrobacterium* which includes a desired recombinant gene. According to the method of the present invention, a seed is infected in an intact state; and no processing is required such as the preparation of a callus of a plant sample to be transformed.

The seed to be infected with an *Agrobacterium* may be a seed on the first day to the third day after sowing. At the time of infection, the seed may already have germinated.

The monocotyledon to be transformed is preferably a plant of the family Gramineae, and more preferably rice (*Oryza sativa* L.). Rice may be Indica rice or Japonica rice.

EFFECTS OF THE INVENTION

According to the present invention, an improved method for transforming a monocotyledon via an *Agrobacterium* is provided. In the method of the present invention, an intact seed of a plant which is intended to be transformed is infected with an *Agrobacterium* containing a desired recombinant gene. By utilizing the present invention, a transformed plant can be created more efficiently and more rapidly.

BEST MODES FOR CARRYING OUT THE INVENTION

Figure 1:
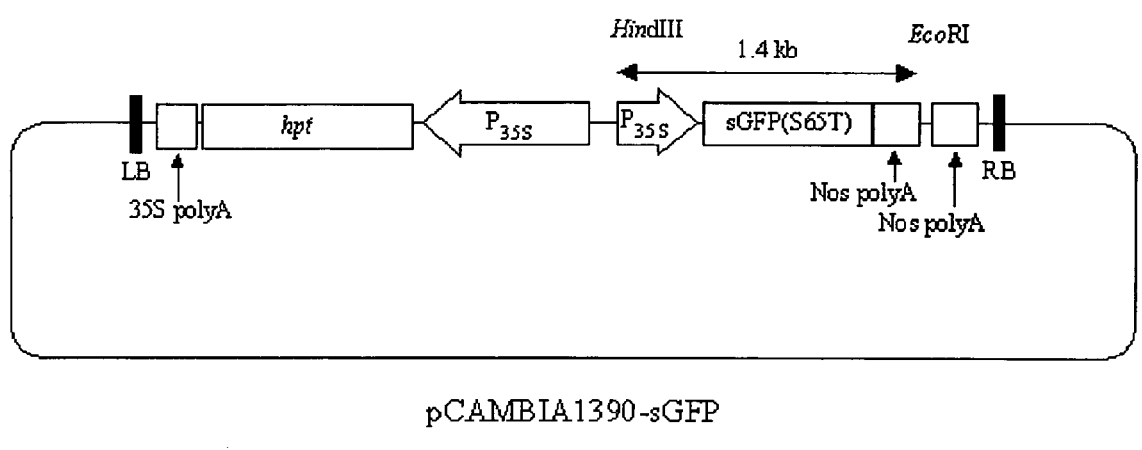
FIG. 1 is a diagram indicating the structure of the binary vector pCAMBIA1390-sGFP, which was used in Example 1 of the present invention.

Hereinafter, the present invention will be described in detail. It should be understood that, in the whole specification, an expression using the singular includes the concept of the plural thereof, unless otherwise specified. Further, it should be understood that a term in the present specification is used in the sense generally meant in the art, unless otherwise specified. Therefore, unless otherwise specified, each of the technical terms and the technological terms used in the present specification has the same meaning as that generally understood by those skilled in the art. If there is an inconsistency, the present specification (including the definitions) should be prioritized.

Definition of Terms

Hereinafter, definition of the terms specifically used in the present specification will be described.

In the present specification, the term "plant growth factor" refers to a factor that promotes growth of plant cells. Examples of plant growth factors include auxins, gibberellins, cytokinins and other plant hormones, although not limited thereto. Examples of auxins include 2,4-D and indoleacetic acid (IAA), although not limited thereto.

The "plants" to which the method according to the present invention is applied to are monocotyledons. Examples of preferable monocotyledons include plants of the family Gramineae (e.g., rice and corn). The most preferable plant to which the method according to the present invention is applicable is rice, and in particular Japonica rice. Unless otherwise indicated, the term "plant" means a plant body and the seeds obtained from a plant body.

Preparation of a Plant Expression Vector

In order to introduce a desired recombinant gene into monocotyledons, an appropriate plant expression vector is constructed which includes the desired recombinant gene. Such a plant expression vector may be prepared by recombinant gene technologies well-known to those skilled in the art. Although pBI-type or pPZP-type vectors are suitably employed to construct plant expression vectors for use in *Agrobacterium* transformation techniques, the plant expression vector is not limited thereto.

A "desired recombinant gene" refers to any polynucleotide which is desired to be introduced into a plant. The desired recombinant gene according to the present invention is not limited to those isolated from nature, but may also include synthetic polynucleotides. Synthetic polynucleotides may be obtained by, for example, synthesizing or modifying a gene having a known sequence by techniques well-known to those skilled in the art. The desired recombinant genes according to the present invention include, for example, any polynucleotide which is desired to be expressed in a plant to be transformed that may be endogenous or exogenous to that plant, or, in the case where it is desired to control the expression of a certain endogenous gene in a plant, a polynucleotide which includes an antisense sequence of a target gene.

Although a desired recombinant gene may contain its own promoter in an operable manner, (i.e., the promoter to which the gene is operably linked in nature) in the case where expression in a plant is intended, the desired recombinant gene may be operably linked to any appropriate promoter, in the case where the gene's own promoter is not contained or where it is desirable that a promoter other than the gene's own promoter be contained. Examples of promoters to be used include a constitutive promoter, a promoter which is selectively expressed in a portion of a plant body, and an inducible promoter.

In the plant expression vector, various regulatory elements may further be linked in such a manner as to be operable within the host plant cells. The regulatory elements may include, preferably, selection marker genes, plant promoters, terminators, and enhancers. It is well-known to those skilled in the art that the type of the plant expression vector to be used and the kinds of regulatory elements may vary depending on the purpose of transformation.

A "selection marker gene" can be used in order to facilitate the selection of transformed plants. Drug resistance genes such as a hygromycin phosphotransferase (HPT) gene for imparting hygromycin resistance, a neomycin phosphotransferase II (NPTII) gene for imparting kanamycin resistance, and a phosphinothricin acetyltransferase (PAT) gene for imparting bialaphos resistance may be suitably employed, although not limited thereto.

A "plant promoter" means a promoter which is operably linked to a selection marker gene and expressed in a plant. Examples of such promoters include cauliflower mosaic virus (CaMV) 35S promoter and nopaline synthetase promoter, although not limited thereto.

A "terminator" is a sequence which is located downstream of a region of a gene which codes for a protein, and which is involved in the termination of transcription when DNA is transcribed to mRNA, as well as the addition of a polyA sequence. Examples of terminators include CaMV35S terminator and the nopaline synthetase terminator (Tnos), although not limited thereto.

An "enhancer" may be employed in order to enhance the expression efficiency of a target gene. As the enhancer, an enhancer region which includes an upstream sequence within the CaMV35S promoter is suitably used. A plurality of enhancers may be employed for each plant expression vector.

Transformation of Plants

The *Agrobacterium* used for the transformation of monocotyledons may be any bacterium of the genus *Agrobacterium*, and preferably *Agrobacterium tumefaciens*. The *Agrobacterium* may be transformed by a plant expression vector containing a desired recombinant gene (e.g., by electroporation). By infecting a seed with the transformed *Agrobacterium*, the desired recombinant gene can be introduced into the plant. The introduced recombinant gene exists in a form integrated within the genome in the plant. The genome in the plant not only means chromosomes in the nucleus, but also includes genome included in various organelles (e.g., mitochondria, chloroplasts) in plant cells.

After removing the husks of the seed of a plant which is intended to be transformed, the seed is pre-cultured in an intact state. A seed being "intact" means that the seed has not been subjected to any artificial manipulations, such as removal of the ovule or scarring of the scutellum.

In the pre-culture, the seeds are sown in a medium (e.g., an N6D medium) containing an appropriate concentration of auxin (e.g., 2,4-D), and may be incubated for typically 1 to 3 days. The temperature during the pre-culture is typically 25° C. to 35° C., and preferably 27° C. to 32° C. After completing the pre-culture, the seeds are sterilized, and thereafter washed thoroughly with water. Next, the seeds may be infected with a transformed *Agrobacterium* under aseptic manipulation.

During infection by the *Agrobacterium* (co-culture), the seeds are incubated in the dark, typically for 2 to 5 days, and preferably for 3 days. The temperature at this time is typically 26° C. to 28° C., and preferably 28° C. Next, in order to eliminate the *Agrobacterium* in the medium, the seeds are subjected to a treatment with an appropriate bacteria eliminating agent (e.g., carbenicillin, Claforan). The transformed seeds are selected on the basis of a selection marker (e.g., drug resistance such as hygromycin resistance).

After the culture under appropriate bacteria-eliminating conditions and selection conditions, the selected transformed seeds may be placed in a redifferentiation medium (e.g., an MS medium) containing appropriate plant regulatory substances, and incubated for an appropriate period of time. In order to allow a plant body to be regenerated, the redifferentiated transformant is placed in a rooting medium (e.g., an MS medium containing no plant regulatory substance). After the growth of roots is confirmed, the transformant may be potted.

The desired recombinant gene which has been introduced into the plant may have action for intended purposes (e.g., expression of a new character of interest, or controlling the expression of certain endogenous genes) within the plant.

It can be confirmed by using well-known techniques whether or not a desired recombinant gene has been introduced into a plant. This confirmation may be made, for example, via Northern Blot analysis. Specifically, the entire RNA is extracted from a leaf of a regenerated plant, subjected to electrophoresis on agarose in a denatured condition, and thereafter blotted on an appropriate membrane. By allowing a labeled RNA probe which is complementary to a portion of the introduced gene to hybridize with the blots, the mRNA of the gene of interest can be detected. Alternatively, in the case where controlling the expression of an endogenous gene in the plant is desired via the introduction of a desired recombinant gene, the expression of the target endogenous gene may be tested, for example, via the aforementioned Northern Blot analysis. If the expression of the target endogenous gene is significantly suppressed as compared to its expression in a non-transformed control plant, it is confirmed that the desired recombinant gene has been introduced into the plant and that the desired recombinant gene has acted to control the expression.

Conventional methods usually require a period of 3 to 4 weeks for inducing dedifferentiation prior to *Agrobacterium* infection. In contrast, the method according to the present invention does not require a step of inducing dedifferentiation, so that the number of days required for creating transformed monocotyledons can be reduced. Furthermore, according to the method of the present invention, it is also possible to reduce the period which is required for selection by conventional techniques, so that it is possible to reduce the influences of culture variation.

In a preferable embodiment of the method according to the present invention, the number of days required for creating a transformation monocotyledon is about 32 days, which is about ⅓ of the number of days (about 90 days) required by conventional *Agrobacterium* transformation methods (see, for example, Example 2 below). Moreover, according to the method of the present invention, a transformation efficiency of 10% to 15% can be obtained in the case of Nipponbare seeds. A similarly high transformation efficiency can also be achieved with other rice cultivars such as Dontokoi or Kitaake. Therefore, by using the method according to the present invention, it is possible to more efficiently and quickly create a transformed plant than by conventional transformation techniques.

EXAMPLE

Hereinafter, the present invention will be specifically described with respect to examples, which do not limit the present invention. The materials, reagents, and the like which are used in the examples are available from commercial sources unless otherwise specified.

Example 1

Transformation of a Rice Plant Using the Method According to the Present Invention Material Transformation was performed according to the following method using Nipponbare, which belongs to the Japonica cultivar.

Sterilization of Seeds

The seeds were sterilized in 70% ethanol for 30 seconds and subsequently in a 2.5% sodium hypochlorite solution for 20 minutes, and thereafter washed with sterilized water.

Vector

A binary vector pCAMBIA1390-sGFP (FIG. 1), which has, on a T-DNA region, a hygromycin-resistant gene that is a marker gene for selecting transformed cells and a GFP (Green Fluorescent Protein) gene that play the role of a reporter for transformed cells, was transformed via *Agrobacterium tumefaciens* EHA105, and was used in the experiment.

Pre-Culture of Rice Seeds to be Infected with *Agrobacterium*

The sterilized rice seeds were sown on an N6D medium (Toki, Plant Molecular Biology Report, 15(1), 1997) containing 2,4-D, pre-cultured at 30° C. under lit condition for 1 to 3 days, and thereafter subjected to *Agrobacterium* infection. The composition of the N6D medium is as follows: 30 g/l of sucrose; 0.3 g/l of casamino acid; 2.8 g/l of proline; 2 mg/l of 2,4-D; 4 g/l of gellite; pH 5.8.

*Agrobacterium* Infection

The rice seeds, which had been pre-cultured for 1 to 5 days as described above, were immersed in an *Agrobacterium* solution. Thereafter, this was placed on a 2N6-AS medium (Hiei et al., The Plant Journal (1994), 6(2), 271-282), and incubated in the dark at 28° C. to effect co-culturing. The composition of the 2N6-AS medium was as follows: minerals and vitamins of N6 (Chu C. C. 1978; Proc. Symp. Plant Tissue Culture, Science Press Peking, pp. 43-50); 1 g/l of casamino acid; 2 mg/l of 2,4-D; 30 g/l of sucrose; 2 g/l of gellite; and 20 mg/ml of acetosyringon. When using 10-40 mg/ml of acetosyringon, the similar result was obtained.

Bacterium Elimination and Selection of Transformed Calluses

After completing the co-culture, by using an N6D liquid medium containing 500 mg/l of carbenicillin, the *Agrobacterium* washed off the pre-cultured seeds. Next, in order to select the transformed cells, the transformed seeds were placed on an N6D medium (selection medium) containing 50 mg/l of hygromycin and 500 mg/l of carbenicillin as agents. The appearance of the transformed cells on the selection medium was evaluated based on the appearance and proliferation of calluses after placement and the expression of the reporter gene, GFP.

Redifferentiation of Transformants

Two weeks after placement on the selection medium, the calluses, which were observed to have proliferated on the selection medium, were placed on a redifferentiation medium (Toki 1997). The composition of the redifferentiation medium is as follows: MS medium (30 g/l of sucrose, 30 g/l of sorbitol, 2 g/l of casamino acid, 2 mg/l kinetin, 0.02 mg/l of NAA, 4 g/l of gellite, pH 5.7) supplemented with carbenicillin (500 mg/l) and hygromycin (50 mg/l).

Potting

The transformants which had redifferentiated were placed on a rooting medium (MS medium containing no hormone, supplemented with hygromycin (25 mg/l)). After the growth of roots was confirmed, the transformants were naturalized.

Southern Blot Analysis Using Regenerated Plant Bodies

Figure 6:
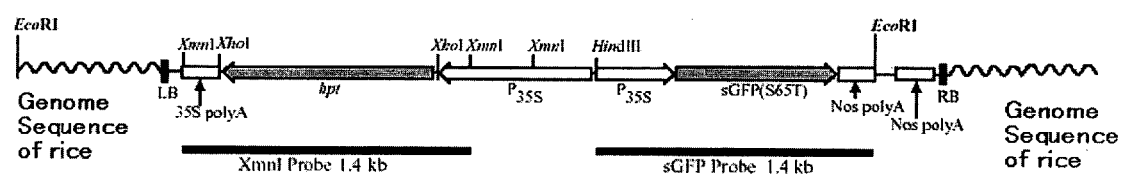
FIG. 6 is a diagram showing a probe used in Southern hybridization.

Genomic DNA was extracted from the leaves of the obtained regenerated plant bodies and the non-transformed plant bodies and subjected to digestion with EcoRI. After that, they were subjected to Southern blot analysis using labeled probes, which was prepared by mixing XmnI probes (1.4 kb) with sGFP probes (1.4 kb) as shown in FIG. 6. The Southern blot analysis was carried out according to the common method (Molecular Cloning, A Laboratory Manual, 2nd edition, Maniatis et al., Cold Spring Harbor Laboratory Press, 1989). As a result, it was shown that plasmid DNA was inserted into a chromosome.

Results

Figure 2:
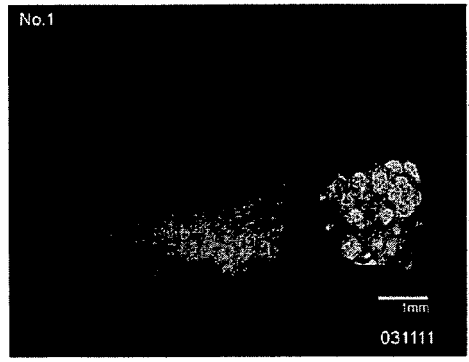
FIG. 2 is a photograph showing a transformant which was obtained by performing transformation using an intact seed that had been pre-cultured for 1 day (upper row: day 7 after selection, middle row: day 14 after selection, and lower row: day 14 after redifferentiation).
Figure 2:
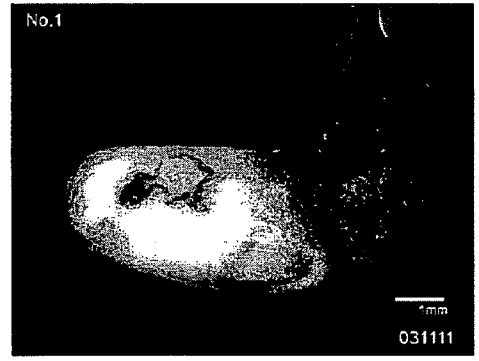
Figure 2:
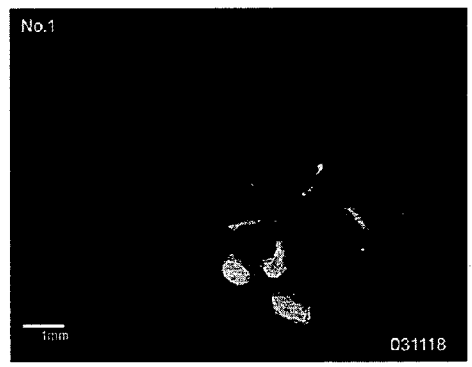
Figure 2:
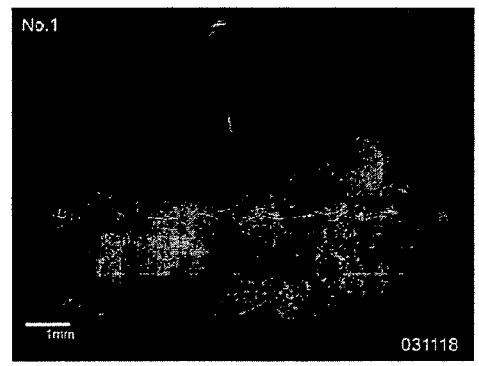
Figure 2:
Figure 2:
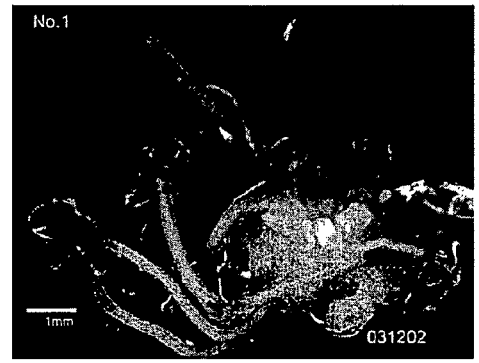
Figure 3:
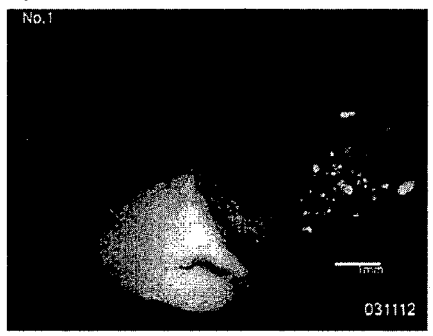
FIG. 3 is a photograph showing a transformant which was obtained by performing transformation using an intact seed that was pre-cultured for 2 days (upper row: day 7 after selection, middle row: day 14 after selection, and lower row: day 14 after redifferentiation).
Figure 3:
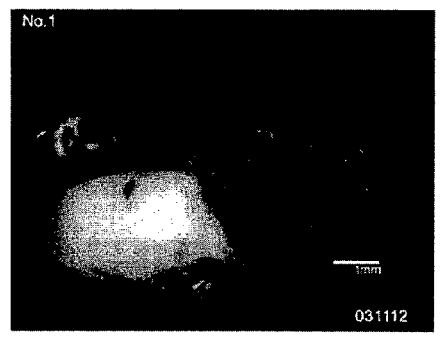
Figure 3:
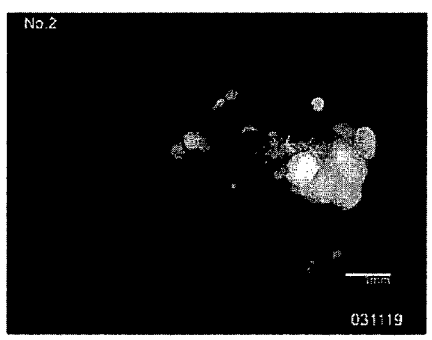
Figure 3:
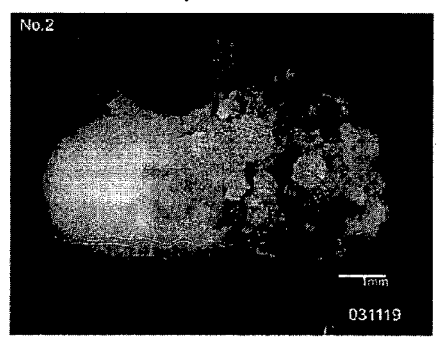
Figure 3:
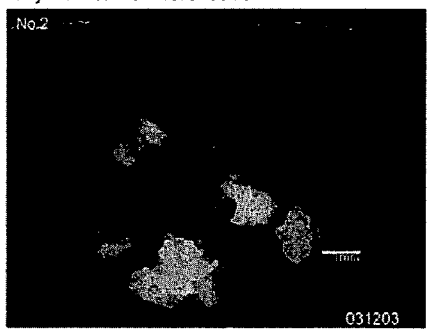
Figure 3:
Figure 4:
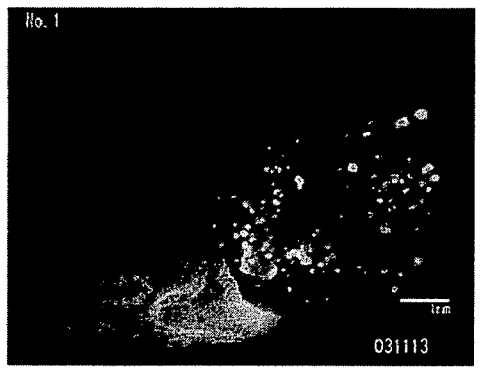
FIG. 4 is a photograph showing a transformant which was obtained by performing transformation using an intact seed that was pre-cultured for 3 days (upper row: day 7 after selection, middle row: day 14 after selection, and lower row: day 20 after redifferentiation).
Figure 4:
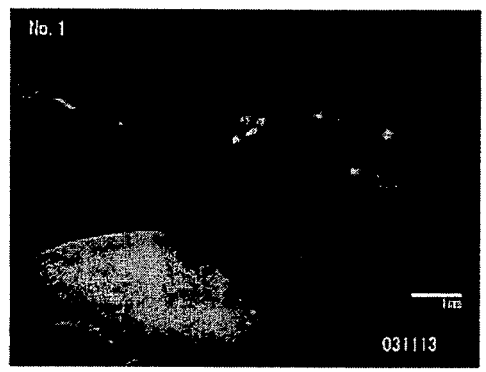
Figure 4:
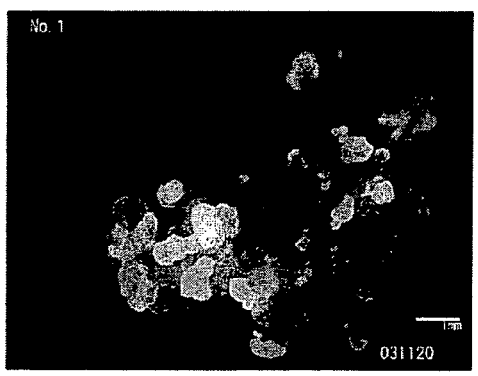
Figure 4:
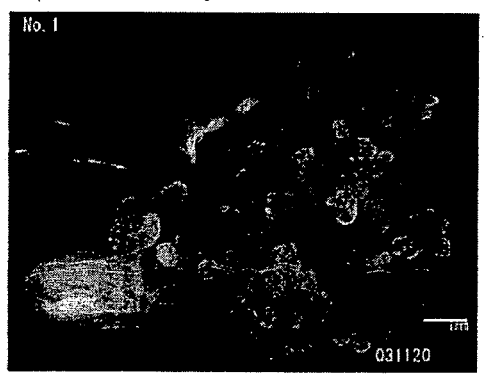
Figure 4:
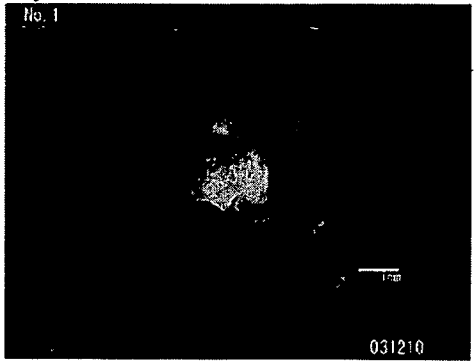
Figure 4:
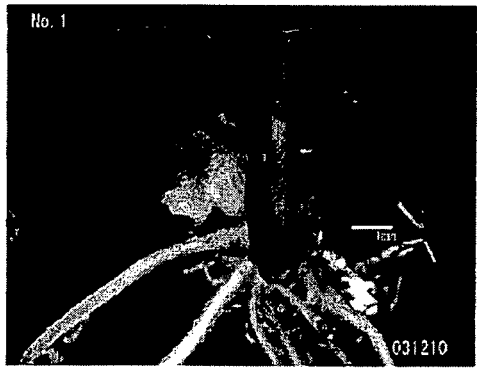

After sowing, the seeds were pre-cultured for 1 day, 2 days, or 3 days. Tissues of the seeds were observed on day 7 and day 14 after selection with an agent (hygromycin), and on day 14 after being placed on the redifferentiation medium. The results are shown in FIGS. 2-4. In each of the drawings, the left panels show the results of observation of GFP fluorescence, and the right panels show tissues observed in natural light. As clarified by these results, tissue which expresses GFP and is resistant to the agent was obtained from all of the intact seeds pre-cultured for 1 day, 2 days, or 3 days after sowing (see the upper/middle rows). Moreover, after culture with the redifferentiation medium, redifferentiated plant bodies were obtained (lower rows). These results mean that the intact seeds, which were pre-cultured for 1 to 3 days, were infected with the *Agrobacterium*, and exogenous genes were introduced into the cells of the seeds.

Figure 5:
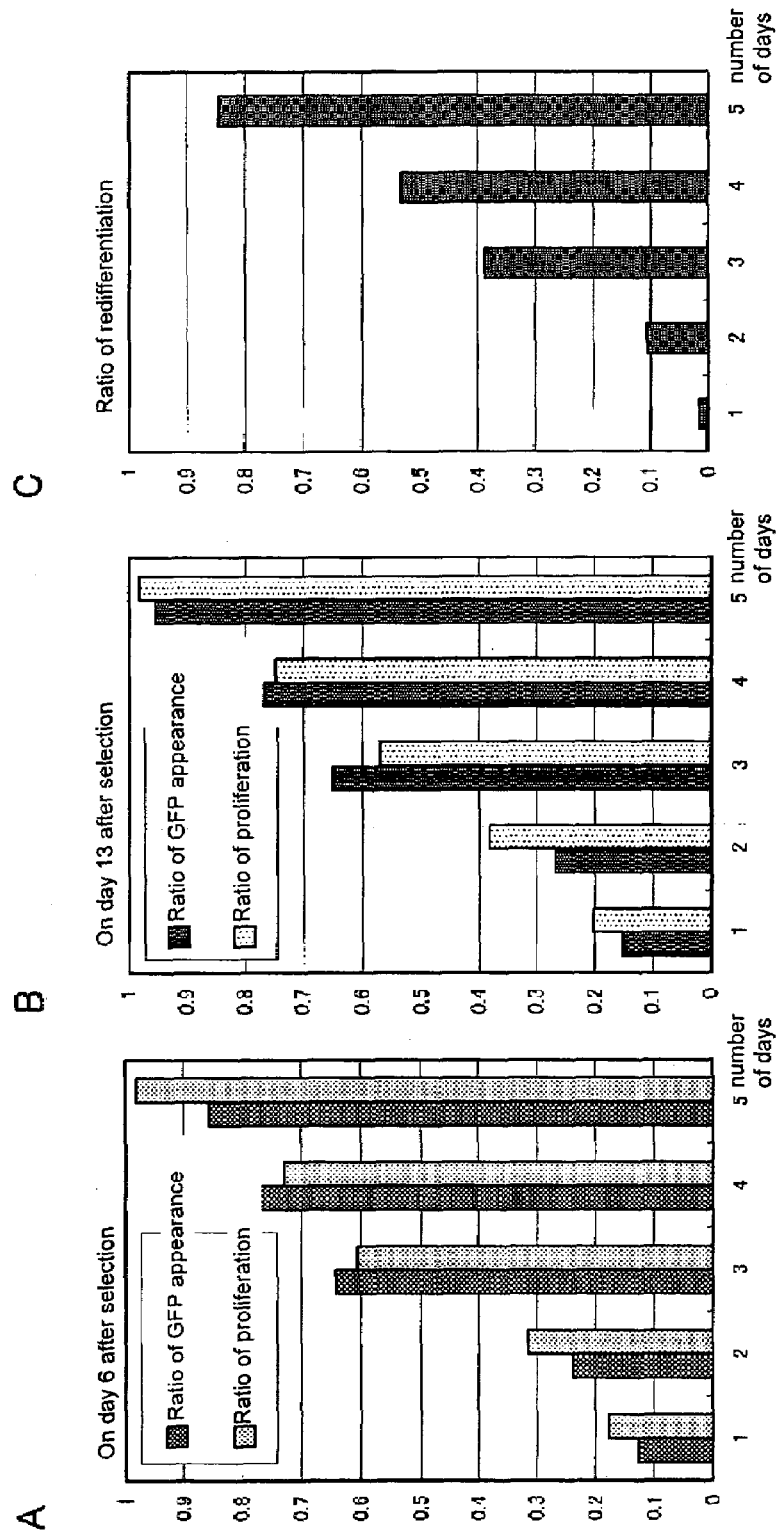
FIGS. 5A and 5B are graphs showing the relationship between the number of days of pre-culture and the ratio of appearance of GFP-expressing tissue (Ratio of GFP expression in the drawings) and the relationship between the number of days of pre-culture and the ratio of appearance of tissue that can be proliferated in the presence of an agent (Proliferation ratio in the drawings), on day 6 (FIG. 5A) and on day 13 (FIG. 5B) after selection.
FIG. 5C is a graph showing the relationship between the number of days of pre-culture and the ratio of redifferentiated plant bodies obtained.

FIGS. 5A and 5B show the results of Example 1 with respect to the relationship between the number of days of pre-culture and the ratio of appearance of GFP-expressing tissue and the relationship between the number of days of pre-culture and the ratio of appearance of tissue that can be proliferated in the presence of an agent. The results shown in FIG. 5 indicate that tissue expressing GFP and tissue that can be proliferated in the presence of an agent appear in the pre-culture by the first day, and that the ratio of appearances thereof increases corresponding to the increase in the number of days of pre-culture.

When the tissue which had been transformed and become hygromycin-resistant was subjected to redifferentiation, 2 clones were redifferentiated in the case of pre-culturing for 1 day (redifferentiation ratio: 1.7%), 11 clones were redifferentiated in the case of pre-culturing for 2 days (redifferentiation ratio: 10.5%), and 44 clones were redifferentiated in the case of pre-culturing for 3 days (redifferentiation ratio: 38.6%). These results indicate that the transformant, which would redifferentiate to the plant body, was obtained by using the intact seed pre-cultured for 1 to 3 days.

FIG. 5C shows the results with respect to the relationship between the number of days of pre-culture and the ratio of redifferentiated plant bodies obtained. The results shown in FIG. 5 indicate that a redifferentiated plant body was obtained by pre-culture for 1 day, and the ratio of appearance thereof increases corresponding to the increase in the number of days of pre-culture.

Further, when Southern blot analysis was carried out using a leaf of the redifferentiated plant body, it was confirmed that an exogenous gene was introduced into a chromosome of the plant cell.

Therefore, by utilizing the method of the present invention, rapid transformation of a plant is enabled.

The invention claimed is:
1. A method for transforming rice, comprising a step of infecting a germinated intact rice seed with an *Agrobacterium* which contains a desired recombinant gene, wherein the seed is germinated by being subjected to pre-culture with a medium containing the growth factor 2,4-D for 1 day after sowing.

* * * * *